United States Patent
Meiksin et al.

(10) Patent No.: US 8,723,673 B2
(45) Date of Patent: May 13, 2014

(54) METHOD AND APPARATUS FOR DETECTION OF STRUCTURE FAILURE

(75) Inventors: Zvi H. Meiksin, Pittsburgh, PA (US); Robert J. Kilgore, Pittsburgh, PA (US)

(73) Assignee: Alertek, LLC, Pittsburgh, PA (US)

( * ) Notice: Subject to any disclaimer, the term of this patent is extended or adjusted under 35 U.S.C. 154(b) by 834 days.

(21) Appl. No.: 12/151,077

(22) Filed: May 3, 2008

(65) Prior Publication Data
US 2008/0278319 A1    Nov. 13, 2008

Related U.S. Application Data

(60) Provisional application No. 60/927,523, filed on May 4, 2007.

(51) Int. Cl.
*G08B 13/00* (2006.01)

(52) U.S. Cl.
USPC ............ 340/566; 340/657; 73/801; 73/570; 73/577

(58) Field of Classification Search
USPC ......... 340/657, 538.12, 538.13, 566; 73/570, 73/577, 587, 645–648, 801
See application file for complete search history.

(56) References Cited

U.S. PATENT DOCUMENTS

| | | | |
|---|---|---|---|
| 3,774,443 A * | 11/1973 | Green et al. ............... 73/577 |
| 4,149,446 A | 4/1979 | Spengler et al. |
| 4,152,929 A | 5/1979 | Edmond et al. |
| RE30,183 E | 1/1980 | Popenoe |
| 4,295,377 A * | 10/1981 | Couchman ............... 73/761 |
| 4,318,302 A | 3/1982 | Choi |
| 4,322,193 A | 3/1982 | Stahl |
| 4,410,296 A | 10/1983 | Unrug |
| 4,601,207 A | 7/1986 | Steblay |
| 5,205,176 A | 4/1993 | Kibblewhite |
| 5,220,839 A | 6/1993 | Kibblewhite |
| 5,329,465 A * | 7/1994 | Arcella et al. ........... 702/184 |
| 5,345,684 A | 9/1994 | Shoup et al. |
| 5,798,981 A * | 8/1998 | Littlejohn et al. .......... 367/13 |
| 6,076,405 A * | 6/2000 | Schoess .................... 73/587 |

(Continued)

FOREIGN PATENT DOCUMENTS

WO    WO 2006/035199    *    4/2006

OTHER PUBLICATIONS

"Reinforcement Analysis and Design of Mechanical Roof Bolting Systems in Horizontally Bedded Mine Roofs," H.Y. Tang and S.S. Peng, Geotechnical and Geological Engineering, vol. 3, No. 1, Mar. 1985.

(Continued)

*Primary Examiner* — Nabil Syed
*Assistant Examiner* — Nay Tun
(74) *Attorney, Agent, or Firm* — Neal P Pierotti; Metz Lewis Brodman Must O'Keefe

(57) ABSTRACT

A detection and alarm system comprises a piezoelectric film sensor and associated circuitry. The sensor detects acoustic emission signals from metallic objects under stress upon which it is affixed. The associated circuitry receives electronic signals from the sensor, creates and evaluates a sensor output value including rate ratio and frequency content of such signals within preset time limits. This data allows the detection of impending failure, an alarm condition, of the metallic object by identifying significant changes in the rate of emission of such sensor signals. An alarm condition may then trigger an alarm signal to warn of such impending failure.

18 Claims, 7 Drawing Sheets

(56) References Cited

U.S. PATENT DOCUMENTS

| | | | |
|---|---|---|---|
| 6,354,152 B1 * | 3/2002 | Herlik | 73/597 |
| 6,399,939 B1 * | 6/2002 | Sundaresan et al. | 250/231.1 |
| 6,826,982 B2 * | 12/2004 | O'Brien et al. | 73/587 |
| 6,995,676 B2 * | 2/2006 | Amacher | 340/602 |
| 7,043,989 B2 * | 5/2006 | Brink et al. | 73/579 |
| 7,080,555 B2 * | 7/2006 | Austin et al. | 73/587 |
| 2005/0017873 A1 * | 1/2005 | Liu et al. | 340/870.01 |

OTHER PUBLICATIONS

"A New Concept for Roof Support," J.C. Stankus and S.S. Peng, Coal Magazine, Sep. 1996.

"Anchorage Pull Testing for Fully Grouted Roof Bolts," C. Mark, C.S. Compton, D.C. Oyler, and D.R. Dolinar, International Conference on Ground Control in Mining, Morgantown, WV, pp. 105-113, Aug. 2002.

"Investigation of Fully Grouted Roof Bolts Installed Under in Situ Conditions," C. Compton and D. Oyler, Proc. of the 24th International Conference on Ground Control in Mining, Morgantown, WV, pp. 302-312, 2005.

"Roof Bolt Response to Shear Stress: Laboratory Analysis," E. McHugh, S. Signer, Proc. of the 18th International Conference on Ground Control in Mining, Morgantown, WV, pp. 232-238, Aug. 1999.

"The Relationship of Roof Movement and Strata-Induced Microseismic Emissions to Roof Falls," A.T. Iannacchione, P.R. Coyle, L.J. Prosser, T.E. Marshall and J. Litsenberger, Minerals Engineering, vol. 56, No. 12, pp. 53-60, Dec. 2004.

"Characteristics of Mining-Induced Seismicity Associated with Roof Falls and Roof Caving Events," A.T. Iannacchione, G.S. Esterhuizen, T.S. Bajpayee, P.L. Swanson and M.C. Chapman, Proc. of the 40th U.S. Rock Symposium, American Rock Mechanics Association, Anchorage, Alaska, pp. 1-10, Jun. 2005.

"Forecasting Roof Falls with Monitoring Technologies—A Look at the Moonee Colliery Experience," A.T. Iannacchione, T.S. Bajpayee and J.L. Edwards, Proc. of the 24th International Conference on Ground Control in Mining, Morgantown, WV, pp. 44-51, Aug. 2005.

"Three Dimensional Microseismic Monitoring of a Utah Longwall," J. L. Ellenberger, K.A. Heasley, P.L. Swanson and J. Mercier, Rock Mechanics in National Interest, vol. II, pp. 1321-1326, Jul. 2001.

"An Analysis of Rock Failure Around a Deep Longwall Using Microseismics," K.A. Heasley, J.L. Ellenberger and P.W. Jeran, 20th International Conference on Ground Control in Mining, Morgantown, WV, pp. 280-286, Aug. 2001.

"Microseismic Activity Associated with a Deep Longwall Coal Mine," K.A. Heasley, J.L. Ellengerger and P.W. Jeran, SME Annual Meeting, Phoenix, AZ, preprint 02-175, pp. 1-5, Feb. 2002.

* cited by examiner

METHOD AND APPARATUS FOR DETECTION OF STRUCTURE FAILURE

CROSS-REFERENCE TO RELATED APPLICATION

The present application claims benefit to U.S. patent application Ser. No. 60/927,523 filed on May 4, 2007.

BACKGROUND OF THE INVENTION

1. Field of the Invention

The present invention relates to acoustic sensing and alarm methods and devices for affixing to support components of a structure. More specifically, the invention relates to a self-managed sensing and alarm system for continuous monitoring of infrastructure structural integrity and deterioration, particularly with respect to assembled structures such as bridges and integrated structures such as bolted support roofs in underground mines.

2. Description of the Prior Art

According to the Mine Safety and Health Administration, 1,500-2,000 reportable roof falls occur each year in underground coal mines in the United States. Roof fall is the primary cause of accidental deaths in underground mines, resulting in dozens of deaths and thousands of injuries every year. According to MSHA reports, 70% of all accidental deaths in underground mines are caused by roof fall. The average cost of such an incident is between $1.5 million and $3.5 million, with an annual cost to the industry in the billions of dollars in lost production, repair, and cleanup.

There are 590,000 highway bridges in the United States. Many of these bridges are aging, posing catastrophic danger to human life in light of the undetected or underdetected impending failures or corrosion of structural components. The present state of the art for the assessment of structural health of bridges depends primarily on visual inspection that can recognize damage only in a late state of deterioration.

Referring to FIG. 1(a), Roof bolts 100 are typically placed four feet apart in order to create support roofs in underground mines. The roof bolts 100 are anchored in the roof 105, as shown in FIG. 1(b), utilizing a settable resin 110 around the bolt and are tightened to hold the various strata 115a, b of the roof 105 together. Less common is the use of an expandable mechanical anchor for anchorage. In either case, support is provided by the tensile load imparted to each bolt upon tightening the bolt head into tight abutment with the mine roof through a mounting plate 120 positioned between the mine roof 105 and the bolt head 125.

A number of prior art methods have been utilized to study and increase beam strength and improve roof support. Nevertheless, in time as mining continues, the strata 115 may start to separate and develop a tensile load on the bolt, as shown in FIG. 1(c). A layer of the strata may also shift horizontally exerting shear stress on the bolt. These forces can result in three different conditions causing roof collapse: (1) the bolt anchorage may fail causing the bolt to slide out of its position, (2) the bolt may fail and eventually break and (3) the roof may crack or separate above the layers held in place by the bolts, known in the art as a cutter roof failure. Statistically, the probability of roof falls in a given mine is 2.5 per year.

Past efforts to predict roof fall have not yielded viable results. A number of prior art references based on bolt loading, tension or strain measurements address the stress-strain relationship in materials. Generally, referring to FIG. 2, as the bolt is loaded or stressed, i.e., put under tension by weight of the overburden 130, typically clay, rock, coal or sand above the mine passage or tunnel, the bolt is strained, i.e., elongated. As shown in FIG. 2, when a critical stress and corresponding strain are reached, the bolt enters the yield region after which it breaks. One prior art approach was to measure the stress or strain, allowing impending bolt breakage to be detected. Experience in the field has shown that these methods are unreliable. Sometimes they predict bolt breakage when the bolt does not break, and at other times they do not predict bolt breakage when bolts do break.

The reason for this failure to predict bolt breakage is inherent in the variable monitored. Not all nominally identical bolts, i.e. identical model number, are in fact identical. The material from which a given batch of bolts is manufactured is not perfectly uniform. There will be certain variations from bolt to bolt. Manufacturing dimension tolerances compound these variations and the unpredictability. Consequently, the stress-strain curves for a given bolt model, in practice, display a spread as shown by area A in FIG. 2. Furthermore, the stress-strain curves for a given single bolt are different for different applied stress histories. In a mine roof, for example, if the bolt is stressed gradually over a long period of time, the curve will be different from a curve associated with spurts of stress over the same period of time, and still different from a curve associated with the same stress levels applied over a different period of time.

Most of the prior art is directed toward the measurement of load, strain or tension on the bolt, and several include the generation of a signal by the measuring device which is propagated within the bolt and the subsequent detection of changes to that signal over time, such as such as Spengler, et al., U.S. Pat. No. 4,149,446, issued Apr. 17, 1979 Popenoe, U.S. Pat. No. 4,114,428, issued Sep. 19, 1978; Choi, U.S. Pat. No. 4,318,302, issued Mar. 9, 1982 and Kibblewhite, U.S. Pat. No. 5,205,176, issued Apr. 27, 1993. Furthermore, the strain in a bolt in response to applied stress is different at different locations along the bolt. While the strain in a bolt is still in the safe zone at one location in the bolt, it may already be at the yield point at another location in the bolt. Installing multiple strain sensors on each bolt would make the system too expensive and measuring strain everywhere along the bolt is entirely impractical. Furthermore, strain data does not necessarily provide the needed information. Shear loading also contributes significantly to bolt failure in roof support in mines, which is not considered at all in load or strain measurements that use load cells, pressure sensitive discs or strain gages.

A different approach to predict roof fall addresses the measurement of roof sagging. Extensometers are used to determine the magnitude, position and rate of movement of soil or rock surrounding an excavation. They are widely used in mining to obtain support design information and as the basis of safety monitoring systems. Extensometers are installed into boreholes and, in mining, the smaller the diameter the better to minimize drilling costs. The simplest form of extensometer makes use of a stainless steel spring reference anchor with a tube indicator attached to it by stainless steel wire and visible at the hole mouth. Movement is indicated by colored reflective bands on the indicator, which are progressively covered as movement develops. In mining, a simple extensometer such as this is known as a "telltale" because it gives a visual indication of roof movement. A large number of such devices would have to be installed to cover a single mine. The National Institute of Occupational Safety and Health developed a Roof Monitoring Safety System that measures roof movement intended for use in wide-open roofs such as in room-and-pillar stone mines. NIOSH admits that this system is not suitable to predict roof fall.

Field use has shown that prediction based on telltale devices is unreliable. Roofs do collapse without prior indication from the device, and sometimes the device indicates an alert to an impending roof fall when the roof keeps staying intact. The failure of the telltale to forecast roof falls is rooted in the quantity that is being measured, i.e., roof sagging. The instrument measures by how much the roof at a given location has sagged relative to a reference point. The reference point is the anchorage location of the instrument that is assumed not to change, a questionable assumption, and furthermore, the instrument does not measure by how much the strata or the structure that holds the strata together has actually weakened.

Sagging of the mine roof results in vertical and horizontal stresses, imparting both axial and shear forces on the roof bolts. Combined tensile and shear forces are at times sufficiently large to cause bolt failure. Whether a bolt fails or not depends on the bolt material, structure and dimensions, on the anchorage resin, on the surrounding rock quality and on the angle between the bolt axis and the direction of the boundary between strata layers. None of these factors are considered or evaluated using the telltale instrument measurements. Therefore, the degree of roof sagging is not a measure of the structural state of the roof and the instrument does not reliably predict roof collapse. Although the strata may have shifted, the structure of the anchored bolts that support the strata may still be perfectly capable of holding the strata together. Alternatively, while roof lowering may be relatively small, the separation between the particular strata may have reached a critical value or the bolt structure that holds the roof together may have weakened to a critical level.

Other prior art methods of detection are based on studies of micro-seismic emission, which deploy geophones over mine roof areas. The geophones upper frequency limit ranges between 4.5 and 14 Hz. High frequencies on the order of hundreds or thousands of kilohertz cannot be detected over large areas because of severe attenuation of high frequency pressure or sound waves. Such systems require the installation of geophones in boreholes in mines and moving or adding them into new boreholes as mining advances. Under this system, in order to determine whether a roof fall is imminent, and its location, it is necessary to combine four computed parameters and apply human interpretation. To date these seismographic studies are unable to reliably predict roof fall. Two problems associated with this approach are that high frequencies cannot be detected and that location determination depends on the speeds of sound wave propagation in various directions. These speeds are not reliably predictable, as they depend on the rock strata's non-homogeneous structures.

In summary, while the need to be able to predict impending roof fall in underground mines or other structural failure in rigid support structures, such as bridges, in time to be able to take proactive action to prevent failure and related injuries is lacking in the art. A system is necessary to identify an alarm condition in time to take proactive action to prevent failure.

SUMMARY OF THE INVENTION

A system is disclosed which places sensors at strategic positions on a given infrastructure and provides an alert alarm when the structure reaches a weakened structural state that requires taking proactive action to prevent infrastructure collapse. The system can be applied to, among other structures, roofs in underground mines and highway bridges. In underground mines, for example, one sensor is preferably placed on each targeted roof bolt head but may be installed on a more limited number of roof bolt heads. When the infrastructure or component weakening reaches a critical level, an alarm, such as a sonic alarm, visible indication, or communication warning, such as a page or computer alert is activated. This may be accomplished by direct electrical connection, an electronic signal which is broadcast by a transmitter sending an alarm signal to a display in a maintenance office or through a communications network such as the internet. Alternatively, the alarm condition may be stored in a memory and extracted upon demand by a receiver device such as in a passive RFID system. As would be apparent to one skilled in the art, any conventional warning or notification system may be utilized.

The sensors preferably utilized in this system respond to acoustic emission, or AE pressure waves from the target metallic material, anchorage resin or overburden, i.e. the surrounding matrix, transmitted through the target metallic material acting as an acoustic waveguide. Conventional AE sensors are typically manufactured of piezoelectric crystals and are associated with a high cost of acquisition and operation. The present system may preferably utilize a much lower cost sensor manufactured of piezoelectric films.

In bridges, sensors can be placed to sense AE transmitted through embedded bolts or steel cables. The signals may, for example, be transmitted by micro-transmitters to a central transceiver installed on the bridge and the central transceiver can transmit the signal by a communications network such as the internet to a computer at a maintenance office or other monitoring station. The sensors and associated electronics may, in order to be cost effective, be energized by solar cells.

When material such as metal, concrete or rock is stressed, it emits acoustic waves generally within a frequency range between tens of kilohertz and a few megahertz. These pressure waves originate from atomic dislocations and micro-cracks as well from cracks propagating into macro-cracks. The waves may be characterized and identified by selection and combination of predictable parameters such as amplitude, frequency, energy, duration and rate of occurrence. As the material approaches a critical zone, such as yield, the rate of AE occurrence increases dramatically.

Many infrastructures contain metal imbedded in other material. As stated earlier, miners install roof bolts of lengths generally between five and twenty feet long, typically in a four feet-by-four feet grid. In pre-stressed concrete highway bridges, reinforcing rods and steel cables are embedded in concrete.

One embodiment of the disclosed system is applied to roof bolts which tie mine roof layers together. Sensors attached to roof bolts detect acoustic emission originating in the bolts, resin, or overburden around and above the bolts. When a critical level of structural deficiency has been reached, the sensor module activates an alarm condition. As referred to in this application, an acoustic wave detected by a sensor and identified as a significant event is called a hit. A critical level of events, or alarm condition, is determined when the hit rate increases dramatically, preferably beyond a preset threshold parameter, e.g., by a factor of 8. Such a rate change indicates that the bolt, surrounding anchorage or overburden has reached a critically weakened point. The sensor converts the pressure wave to a voltage that is processed by an electronic circuit. In the preferred embodiment, the voltage waveforms that represent the pressure waves or hits, are envelope-detected and the number of envelopes per given time interval are counted and a sensor output value is computed. This is preferably the ratio between the measured or detected number of hits for a particular time interval and a baseline reference value, entered in memory. The baseline reference value is an average obtained over an initial, preset time period when the bolt is first installed. The detection of any of these conditions causes the hit rate to increase at a rate beyond a preset threshold and an alarm condition is identified.

Examples of alarm indicators are visible indicators, such as LEDs that turn on or an RF transmitter that emits a warning signal. In practice, a situation that requires immediate action may be defined based on patterns associated with the alarm indicators. For example, a single lit LED may not cause concern because the roof weight may be taken up by neighboring bolts. Similarly two lit LEDs several neighbors apart may not be of concern. On the other hand, three immediate neighboring lit LEDs, for example, may require immediate action to prevent roof collapse.

When RF transmitters are used, they may communicate with the mine communications network, and be transmitted, for example, to the maintenance crew office below or above ground and a pattern can be displayed on a video terminal. Algorithms which include preset thresholds for the various parameters allow a computer to automatically determine whether immediate action is needed or not.

Some distinguishing properties of this system are: (1) the location of the infrastructure weakening area is not determined by a triangulation technique and human judgment, but directly by the sensor location indicated by an LED or video monitor; (2) the infrastructure weakening is not measured in terms of "typical" or "average" values that miss alarm states, or cause false alarms, but the measurement is self referenced; and (3) the film sensors are very inexpensive relative to traditional sensors.

These and other advantages and features of the present invention will be more fully understood upon reference to the presently preferred embodiments thereof and to the appended drawings.

DETAILED DESCRIPTION OF THE PREFERRED EMBODIMENTS

Figure 1:
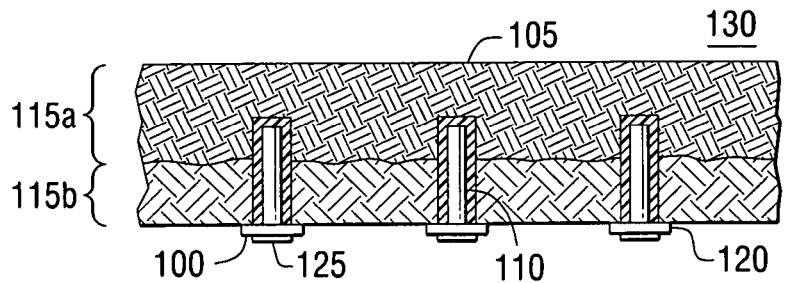
FIG. 1(a) is a diagrammatic plan view of an underground mine roof bolt arrangement of the prior art.
FIG. 1(b) is a sectional view of the roof bolts of FIG. 1(a) taken along line I(b)-I(b).
FIG. 1(c) is a prior art sectional view of roof bolts under stress.
Figure 1:
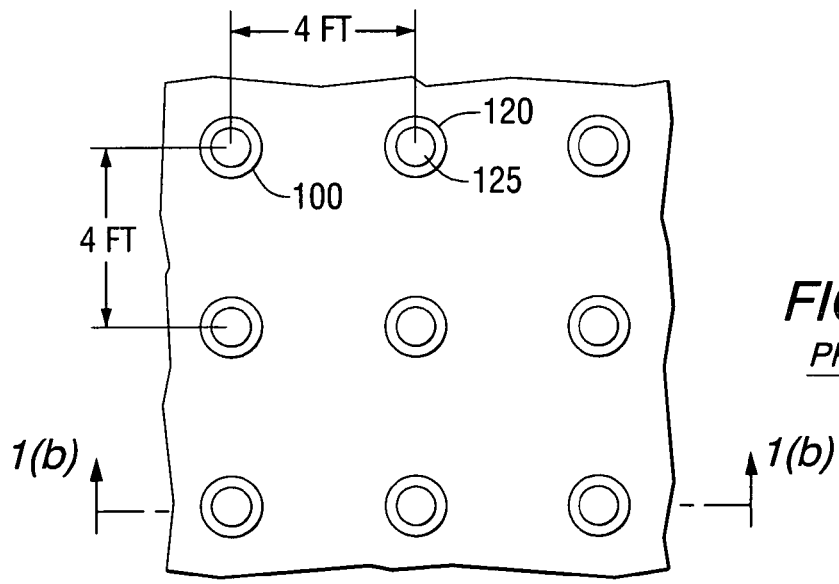
Figure 1:
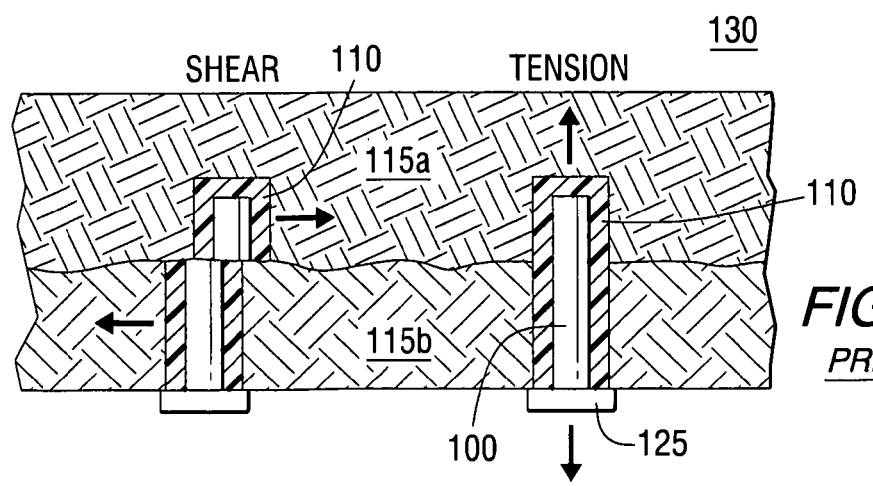
Figure 2:
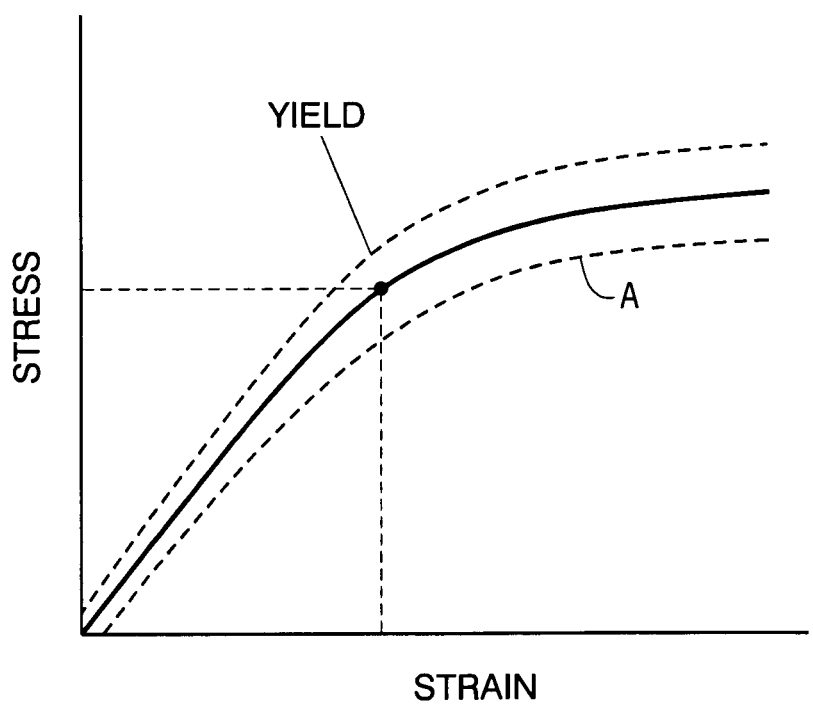
FIG. 2 is a diagrammatic view of a stress/strain graph of a roof bolt of the prior art.
Figure 3A:
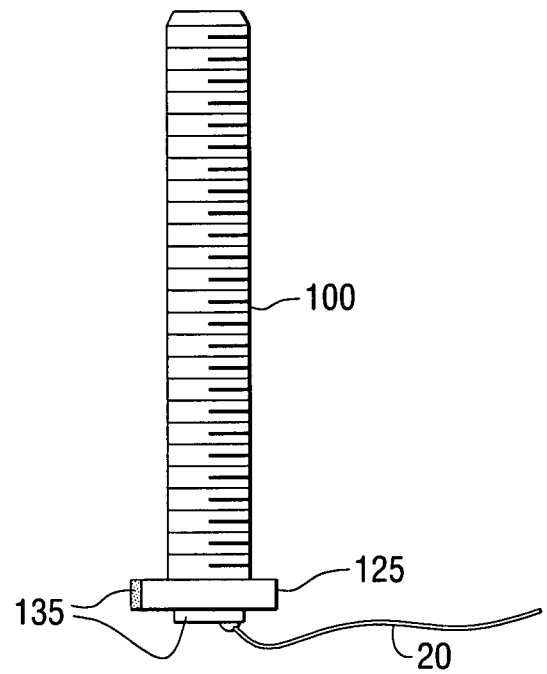
FIG. 3 is a top plan and side view of a roof bolt having a sensor of the present invention mounted thereon.
Figure 3B:
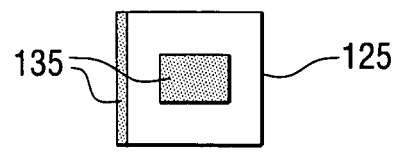
Figure 4:
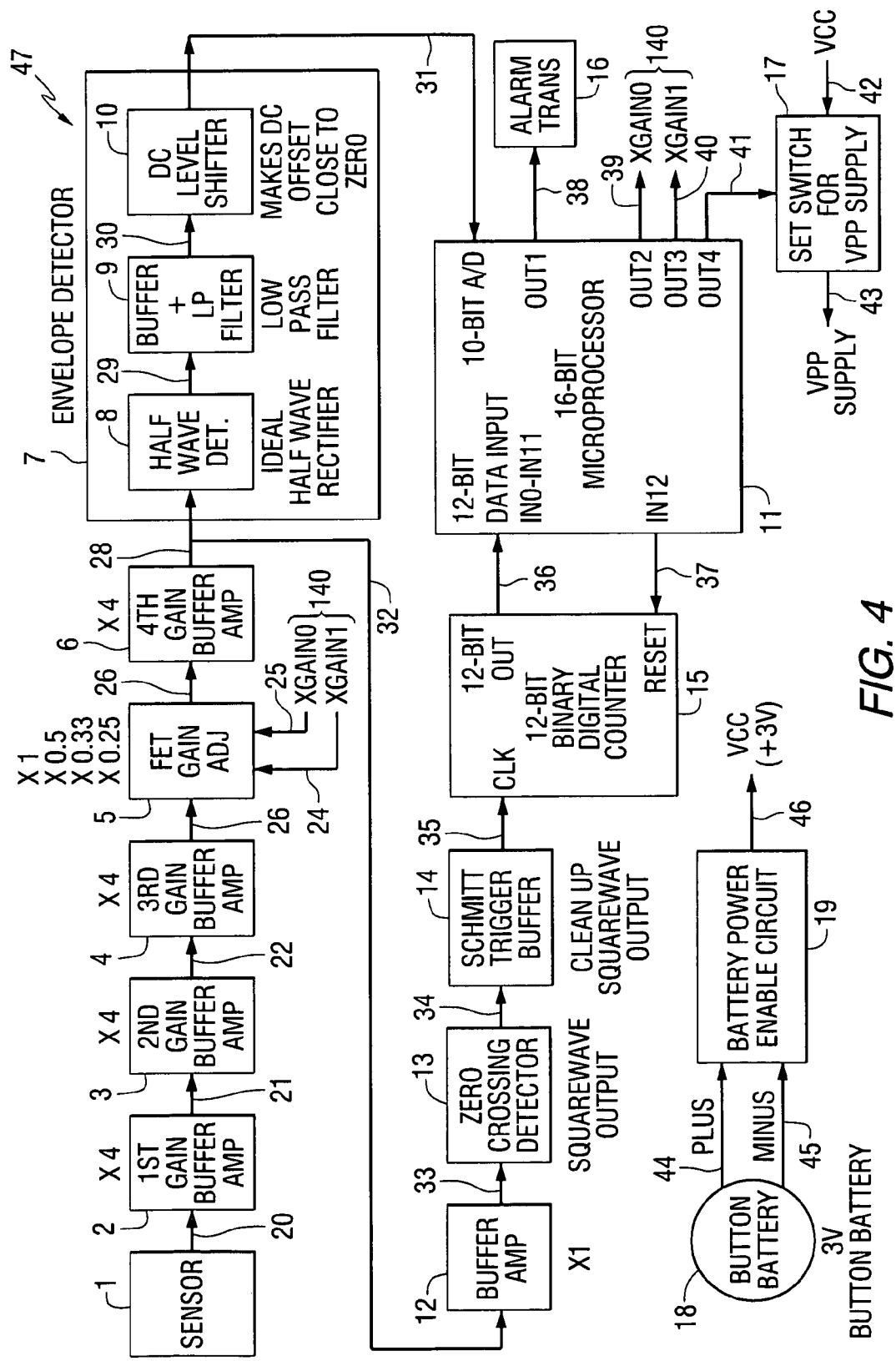
FIG. 4 is a diagrammatic view of the electronic circuitry of one embodiment of the present invention.

Referring now to FIGS. 3 and 4, one embodiment of the system 47 illustrates a sensor device 135 attached to the head 125 of a roof bolt 100. The sensor device 135 may contain an AE sensor 1 alone, together with a transmitter (not shown) for wireless communication to the remainder of the system, a sensor lead 20 for wired electronic communication to the remainder of the system, or may contain the entire system in a discrete housing. The AE sensor 1 may be constructed of a piezo film sensor such as the LDTO-028K/L sensor, manufactured by Measurement Specialties, Inc.

Referring now to FIG. 4, sensor 1 sends the output signal through sensor line 20 to buffer amplifier 2. The buffer stage is desirable because the sensor has high output impedance. Buffering the output makes the signal less susceptible to noise. The buffered signal is transmitted through line 21 to amplifier 3. The output signal from amplifier 3 is transmitted through line 22 to amplifier 4 where it is further amplified. The signal is then sent through line 26 to an automatic gain control amplifier 6. The gain is controlled through gain input signals 140 entering AGC amplifier 6 through lines 24 and 25. The gain input signals 140 for AGC amplifier 6 are transmitted from microprocessor 11 through lines 39 and 40 to FET gain adjustment circuit 5. The microprocessor 11 adjusts the gain for AGC amplifier 6 based on the envelope amplitude that it detects through line 31 from the output of envelope detector circuit 7, as will be described below. The envelope detector circuit 7 consists of half wave rectifier 8, buffer and low pass filter 9, and DC level shifter 10. The output from FET gain adjustment circuit 5 feeds into amplifier 6 through line 26. AGC amplifier 6 sends its output signal through line 28 to buffer and low pass filter 9 through line 29. The output of buffer and low pass filter 9 send its output signal through line 30 to DC level shifter 10. The DC level shifter is used so that the envelope detector circuit 7 output is read by microprocessor 11 only if the envelope detector circuit 7 output signal is above a certain threshold, for example 0.2 volts. This is needed in order not to mistake noise for signal. Prior to entering DC level shifter 10, the signal has an offset of one half of the battery voltage because of the use of a single battery supply. Level shifter 10 adjusts the threshold level to the desired value.

AGC amplifier 6 sends its output signal also to buffer amplifier 12 through line 32. The output from buffer amplifier 12 enters zero crossing detector 13 through line 33. Each zero crossing of the output signal from AGC amplifier 6 triggers Schmitt trigger buffer through line 34. Schmitt trigger buffer 14 connects to digital counter 15 through line 35 causing digital counter 15 to count the number of zero crossings of the signal coming from the output of AGC amplifier 6. The count in digital counter 15 is transmitted to microprocessor 11 through line 36. When digital counter 15 reaches a predetermined value, a signal is output through line 37 from microprocessor 11 to reset the digital counter 15.

As is clear from the description above, signal waveform output of sensor 1 can be closely reproduced from the envelope and zero crossing information in microprocessor 11. How the information is used will become clear with reference to FIG. 5 and its associated description, below.

To preserve battery energy, the system may be put at certain times, to be defined below, into an inactive or sleep mode. This is controlled by microprocessor 11 through line 41 that connects to inactive mode switch 17. When inactive mode switch 17 is closed, battery voltage VCC is applied as the supply voltage VPP to system 47. Battery 18 has its positive and negative terminals connected, respectively, through lines 44 and 45 to battery power enable circuit 19. This prevents battery 18 from excessive discharge when system 47 is not in use. Battery power enable circuit 19 is enabled when system 47 is made ready for use. When battery power enable circuit 19 is enabled, the output voltage of battery 18 is applied to system 47 through line 46.

In operation, microprocessor 11 receives signal information originating in acoustic sensor 1. The information received includes envelopes of the acoustic signal, which are typically in the 600 μs to 2 ms range and threshold crossings of the acoustic signal. Based on this information, microprocessor 11 determines when an alarm condition has been reached as will be illustrated further with respect to FIG. 5. In addition, microprocessor 11 performs power management functions so that maximum battery life is achieved. System 47 will be placed in an inactive mode much of the time. Periodically, dependent on the detected acoustic emission activity in the previous active mode, system 47 will resume function, take readings, determine if alarm conditions are present and, if appropriate, return to the sleep mode as will be illustrated with reference to FIGS. 5 and 6, below. System 47 may include alternative embodiments without changing its essential functioning. For example, buffer amplifiers 2, 3 and 4 can be replaced with a single amplifier. Three amplifiers are preferably used to obtain both high gain and broad bandwidth. Obtaining the same features in a single amplifier is much more expensive and causes much higher energy use causing quicker battery drain. As another example, the zero crossing count in microprocessor 11 can be used to separate output signals, e.g., of 300 kHz from signals of 700 kHz. Similar information can be obtained by inserting two band-pass filters in parallel, before the input to envelope detector circuit 7. Band-pass filters may be employed to reduce the amount of electromagnetic information which must be processed. For example, a first, or low frequency range band pass filter between 100 kHz and 300 kHz and a second, or high frequency range band pass filter between 350 kHz and 700 kHz may be applied to filter the voltage coming from the sensor output. Output signal from both frequency ranges indicate that AE is coming from the bolt itself. An output signal from only the low frequency range indicates that the bolt anchorage has weakened either because the anchorage resin has deteriorated to a critical level, or the overburden has cracked to a critical level.

Figure 5:
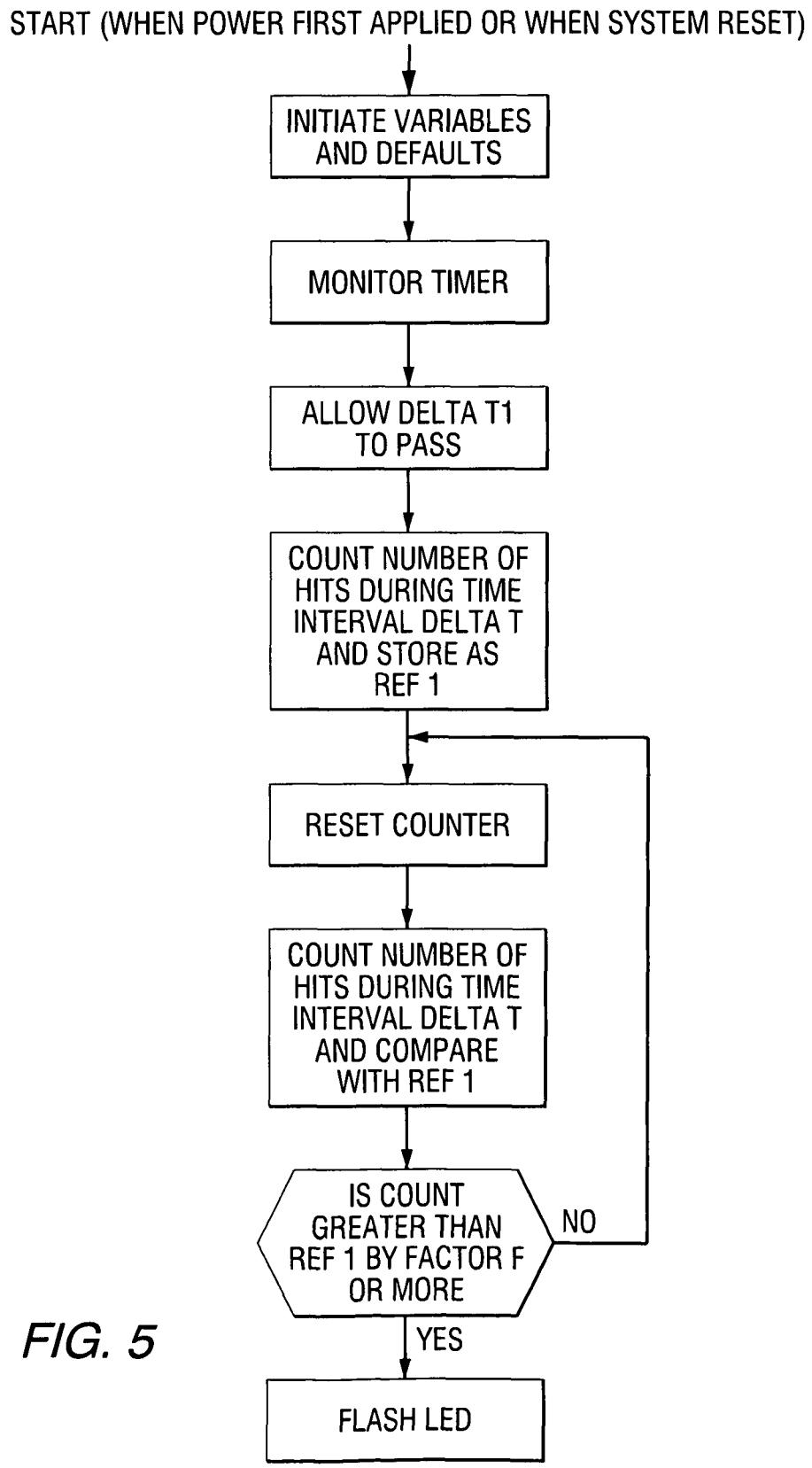
FIG. 5 is a diagrammatic view of a decision tree illustrating a first embodiment of the logic of the electronic circuitry of the present invention.
Figure 7:
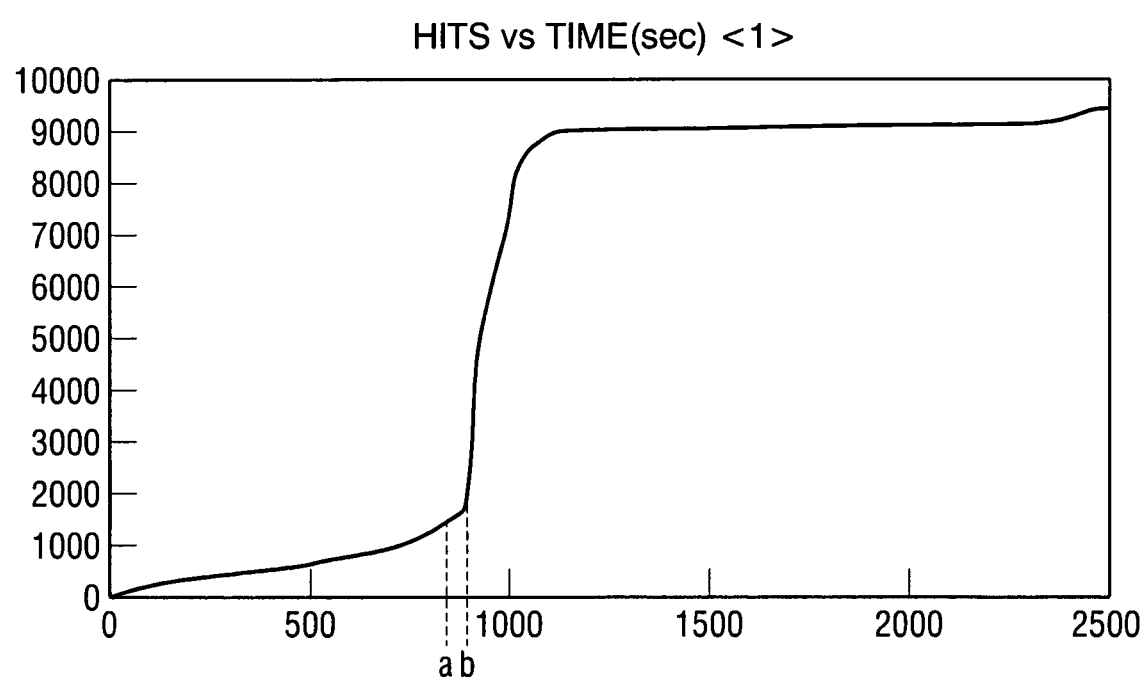
FIG. 7 is a graph view of the calculation of the sensor output value over time.

Several different embodiments may be implemented in terms of procedures as expressed by way of software and executed by microprocessor 11. FIG. 5 illustrates the preferred methodology. When power is first turned on for system 47, the variable and default values of microprocessor 11 are initiated including setting values for DELTA T1, DELTA T and threshold variable F. A time period DELTA T1 is allowed for the system that is being monitored to settle before the acoustic emission hit count is detected. In a mine roof embodiment, for example, when a roof bolt is first installed in the roof, it takes time for the roof bolt and resin structure to settle in the rock strata, causing unique acoustic emission signals during this transition period. After period DELTA T1 has elapsed, the number of hits during a time interval DELTA T is counted and stored in memory as variable REF 1. This establishes the baseline reference value for all further measurements. In the mine roof embodiment, a baseline is established for each particular bolt in the roof structure. The counter is reset and a new count of hits during each time period DELTA T is made. The number of counts is compared with the value REF 1 for each time period DELTA T to create a sensor output value curve, as shown in FIG. 7, which may be a rate ratio, a frequency measurement or other calculated value as identified elsewhere in this application. FIG. 7 is a graph of hit values against time and particularly illustrates a bolt being exposed to increasing stress. The graph line undergoes a significant shift in slope between points a and b and the ratio of measured hits to the baseline value within this range exceeds the threshold of 8, set as REF 1. When the count is less than the value REF 1 by a preferred factor of 8, then the counter is reset after which a new hit count is begun. If the count is greater than the value REF 1 by a factor of 8 or more, then an alarm condition is identified and an alarm signal is transmitted to the users through line 38, as shown in FIG. 4 to alarm/transmitter 16. This may be by a visual indicator such as a flashing LED. Alternatively, the device may transmit an alarm signal through a transmitter well known to those skilled in the art to a remote location where the alarm would be sounded or displayed. The alarm condition is identified and an alarm signal is generated when the object being monitored has reached a significant degree of weakening. In the roof bolt example, the material yield point would have been reached.

In this example, comparing the number of hits counted during a fixed time interval with a reference value identified the alarm condition. Another way to identify the alarm condition is to take the derivative of the cumulative hit count. Under safe conditions, the slope of the cumulative hit curve, when plotted, has a nearly constant slope. When the yield zone of material is entered the slope increases dramatically and soon reaches a new, higher, nearly constant slope. Microprocessor 11 can thus compute the derivative of the cumulative hit count and determine the alarm level when the derivative increases by a factor of five, for example. To avoid errors caused by minor fluctuation in slope, the derivative can be averaged over short periods of time.

In an alternative embodiment, the signal frequency of each hit can be monitored. A shift from a high frequency content of 600 kHz, for example, to a low frequency content of 300 kHz, for example, would indicate that the anchorage or strata around the bolt has weakened to a degree that identifies an alarm condition. This can be accomplished by inserting two band-pass filters in system 47, or by monitoring the threshold cross over in microprocessor 11 as described above. Alternatively, the hit rate and the frequency of the acoustic emission can be monitored and the OR function can be utilized to identify an alarm condition when either of these measurements indicate that the danger zone has been entered.

Figure 6:
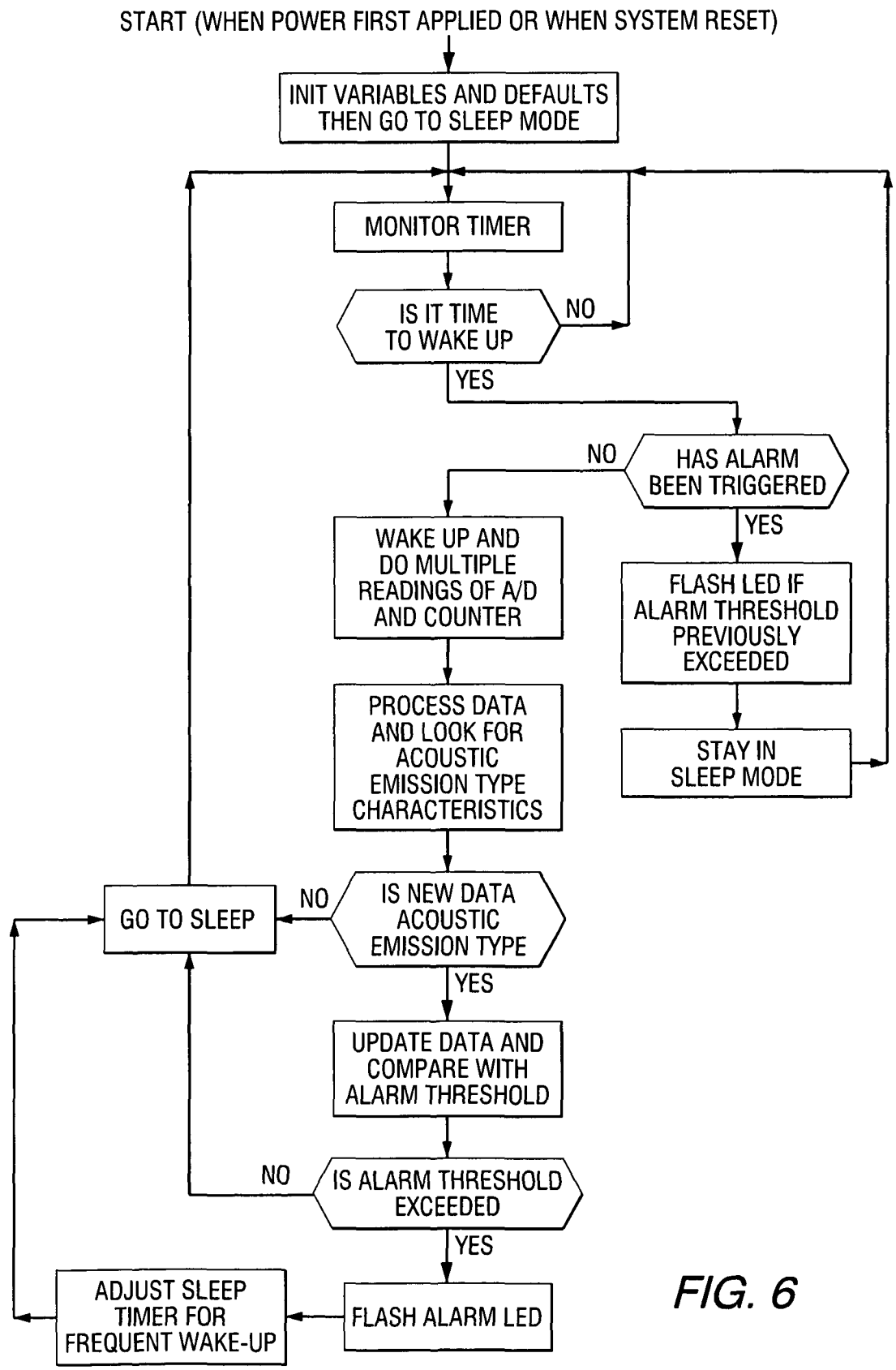
FIG. 6 is a diagrammatic view of a decision tree illustrating a second embodiment of the logic of the electronic circuitry of the present invention.

FIG. 6 illustrates an embodiment of an energy saving mode. System 47 is fully powered up only at certain time intervals during which periods readings are taken. In order not to miss important events, the inactive period length is adaptable and varies dependent on values obtained when the last readings were taken. When the readings are benign, the inactive period is set for a longer interval. When the readings show a high degree of variability of data input or signals detected, the inactive period is set for a shorter interval. The program expressed by the flow chart of FIG. 6 includes a second energy saving feature. Instead of having an alarm signal, such as an LED flash, be transmitted continuously after an alarm condition has been detected, the alarm signal is discontinued turns off after one or several preset cycles and the timer is set for frequent wake up. In the following cycle, when the decision box HAS ALARM BEEN TRIGGERED, the output will be "YES" and the alarm signal, such as the LED flash is triggered again and the system goes back to inactive mode and the system goes back to the MONITOR TIMER box. After an alarm has been activated once, the cycling path is much shorter than the cycling path taken before an alarm condition was indicated, saving even more energy.

Another feature of embodiment illustrated in FIG. 6 is the box PROCESS DATA AND LOOK FOR ACOUSTIC EMISSION TYPE CHARACTERISTICS. Using signal envelope and threshold cross over information and comparison with previous reading results, the program will determine if the signal actually caused by acoustic emission. This step is particularly useful if the environment is very noisy. Persons skilled in the art, can easily add features such as low-battery indicator and certain LED flashing patterns to indicate that system status.

While a present preferred embodiment of the invention is described, it is to be distinctly understood that the invention is not limited thereto, but may be otherwise embodied and practiced with the scope of the following claims.

What is claimed is:

1. A detection system for identifying deterioration in one of a plurality of target metallic objects and their surrounding matrix comprising:
   acoustic sensors affixed to a plurality of said target metallic objects which receive acoustic emission waves emitted directly from stresses within said target metallic objects and the immediately adjacent surrounding matrix;
   a detection circuit in electronic communication with said acoustic sensors which identifies said acoustic emission waves;
   an analysis circuit in electronic communication with said detection circuit which determines whether changes in the rate of said acoustic emission waves have met a preset threshold for the location of said at least one of said target metallic objects, wherein a hit is said acoustic emission wave that is identified as a significant event and wherein a plurality of said hits are detected, and wherein the determination of whether changes in the rate of said acoustic emission waves have met a preset threshold involves the counting of said hits;
   wherein said preset threshold is calculated by determining a baseline reference value obtained from said acoustic emission waves emitted directly from stresses within said target metallic object and the immediately adjacent surrounding matrix during a preset time period after installation of said target metallic object and before monitoring for deterioration in said target metallic object and the immediately adjacent surrounding matrix; and
   an alarm circuit in electronic communication with said analysis circuit for transmitting an alarm signal when said preset threshold has been met identifying the location of said at least one target metallic objects which has exceeded said threshold.

2. A detection system as described in claim 1 wherein said acoustic sensor is constructed of piezoelectric film.

3. A detection system as described in claim 1 wherein the alarm signal is visual.

4. A detection system as described in claim 1 wherein the alarm signal is auditory.

5. A detection system as described in claim 1 wherein the alarm signal is transmitted to a remote location.

6. A detection system as described in claim 5 wherein said plurality of acoustic sensors are in electronic communication with a remote monitoring location.

7. A detection system as described in claim 1 wherein said detection circuit further comprises at least one signal filter.

8. A detection system as described in claim 7 wherein said at least one signal filter is selected from the group comprising a low pass filter and a high pass filter.

9. A detection system as described in claim 1 wherein said analysis circuit further comprises at least one of a digital counter and a zero crossing detector.

10. A method for identifying deterioration in one of a plurality of target metallic objects or their surrounding matrix comprising:
    affixing acoustic sensors to a plurality of said target metallic objects which receive acoustic emission waves emitted directly from stresses within said target metallic objects and the immediately adjacent surrounding matrix;
    identifying changes in the rate of said acoustic emission waves from said sensors to determine if a preset threshold value in the location of said at least one of said target metallic objects has been exceeded to determine whether an alarm condition is present, wherein a hit is said acoustic emission wave that is identified as a significant event and wherein a plurality of said hits are detected, and wherein the determination of whether the preset threshold value in the location of said at least one of said target metallic objects has been exceeded involves the counting of said hits;
    wherein said preset threshold value is calculated by determining a baseline reference value obtained from said acoustic emission waves emitted directly from stresses within said target metallic object and the immediately adjacent surrounding matrix during a preset time period after installation of said target metallic object and before monitoring for deterioration in said target metallic object and the immediately adjacent surrounding matrix; and
    transmitting an alarm signal when said alarm condition is present.

11. The method of claim 10 wherein the alarm condition is present when a ratio of changes between the rate of acoustic emission waves and the baseline reference value exceeds a factor of 8.

12. The method of claim 11 wherein the acoustic emission waves are detected by identifying the zero crossing characteristics of said acoustic emission waves.

13. The method of claim 12 wherein said acoustic emission waves are converted to a voltage.

14. The method of claim 10 wherein identifying changes in the rate of said acoustic emission waves is determined from hit rate ratios.

15. The method of claim 10, further comprising the step of identifying the nature of the impending failure of the metallic target object from the frequency range of the acoustic emission waves.

16. The method of claim 10, further comprising the step of periodically suspending the detection step for a second preset time period.

17. The method of claim 16, wherein said second preset time period is variable.

18. The method of claim 17, wherein said variability of said second preset time period is determined by the sensor output value calculated from said acoustic emission waves.

* * * * *